United States Patent [19]
Dau

[11] 4,290,308
[45] Sep. 22, 1981

[54] METHOD OF MONITORING DEFECTS IN TUBULAR PRODUCTS

[75] Inventor: Gary J. Dau, Palo Alto, Calif.

[73] Assignee: Electric Power Research Institute, Inc., Palo Alto, Calif.

[21] Appl. No.: 76,483

[22] Filed: Sep. 17, 1979

[51] Int. Cl.³ .............................................. G01N 29/04
[52] U.S. Cl. ........................................ 73/602; 73/628
[58] Field of Search ................................. 73/602, 628

[56] References Cited

U.S. PATENT DOCUMENTS

| | | | |
|---|---|---|---|
| 3,662,589 | 5/1972 | Adler et al. | 73/602 |
| 3,991,607 | 11/1976 | Niklas | 73/602 |
| 3,996,791 | 12/1976 | Niklas et al. | 73/602 |
| 4,052,889 | 10/1977 | Mucciardi et al. | 73/602 |

*Primary Examiner*—James J. Gill
*Attorney, Agent, or Firm*—Flehr, Hohbach, Test

[57] ABSTRACT

A defect such as a crack in a steam pipe is monitored by employing ultrasonic techniques to generate defect dependent signals and employing an Adaptive Learning Network (ALN) model to analyze the signals, whereby changes in the defect can be detected.

3 Claims, 6 Drawing Figures

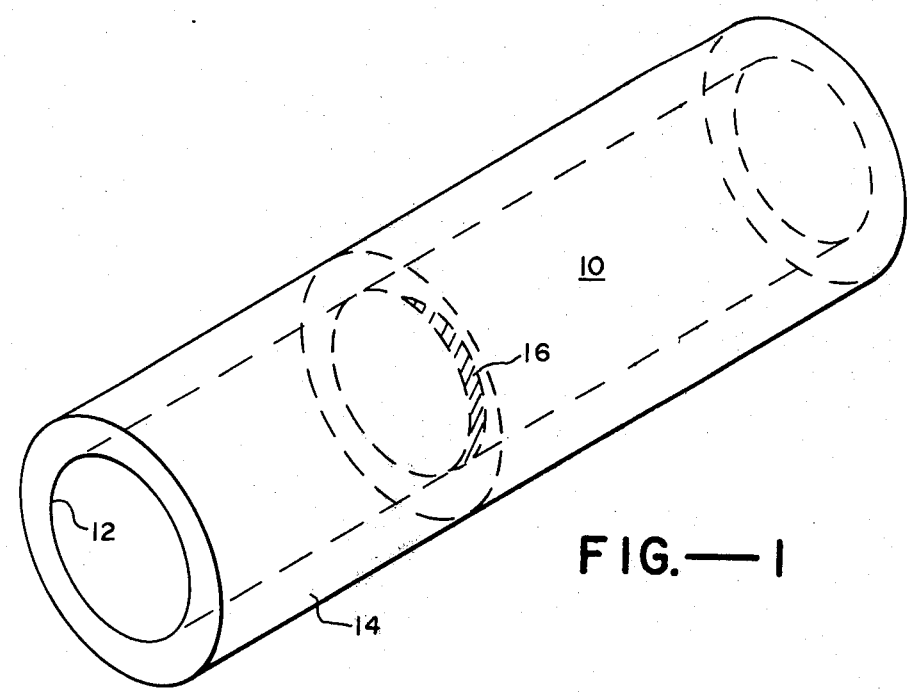
FIG.—1
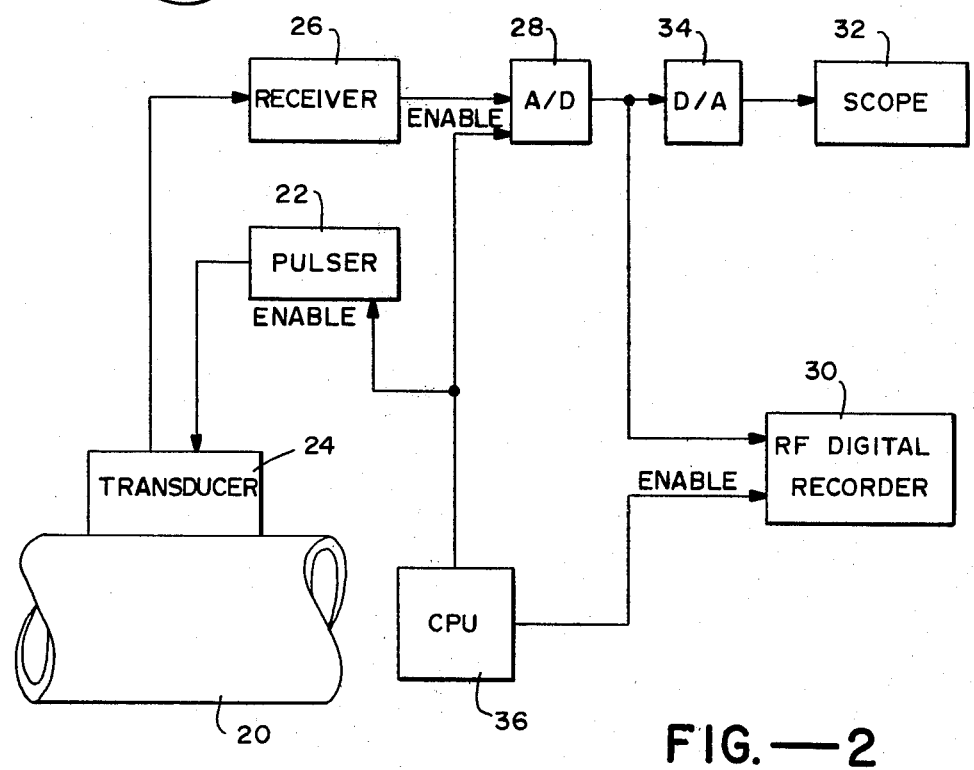
FIG.—2

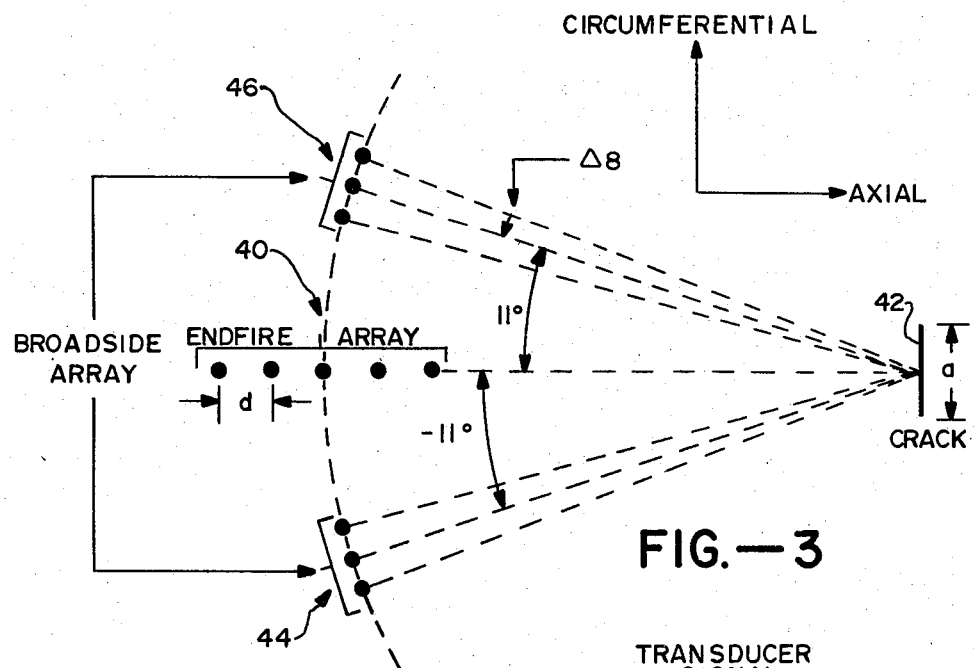
FIG.—3
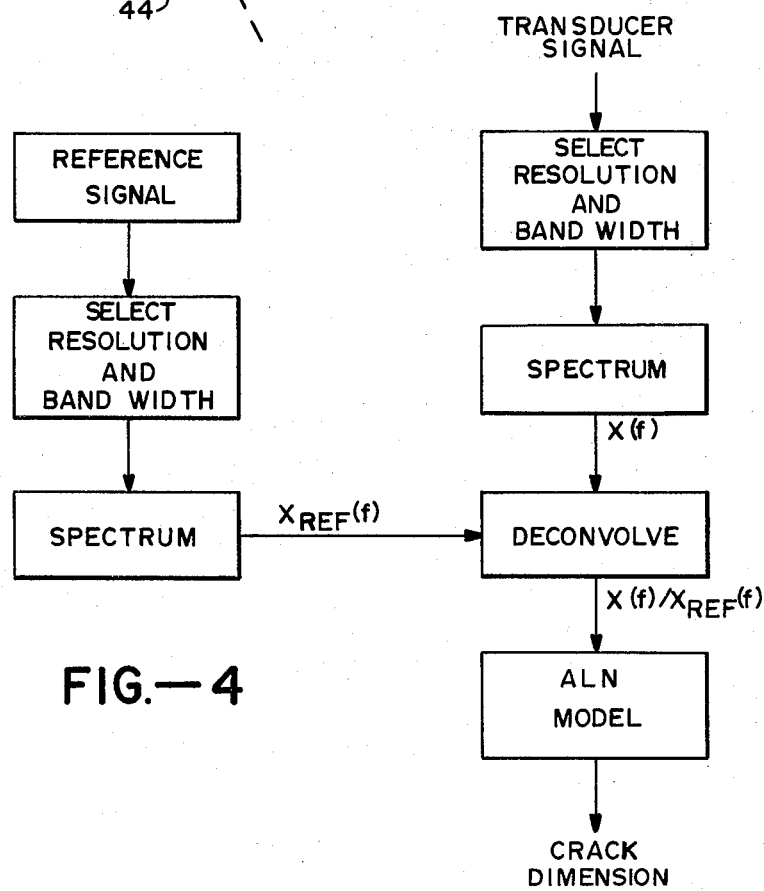
FIG.—4

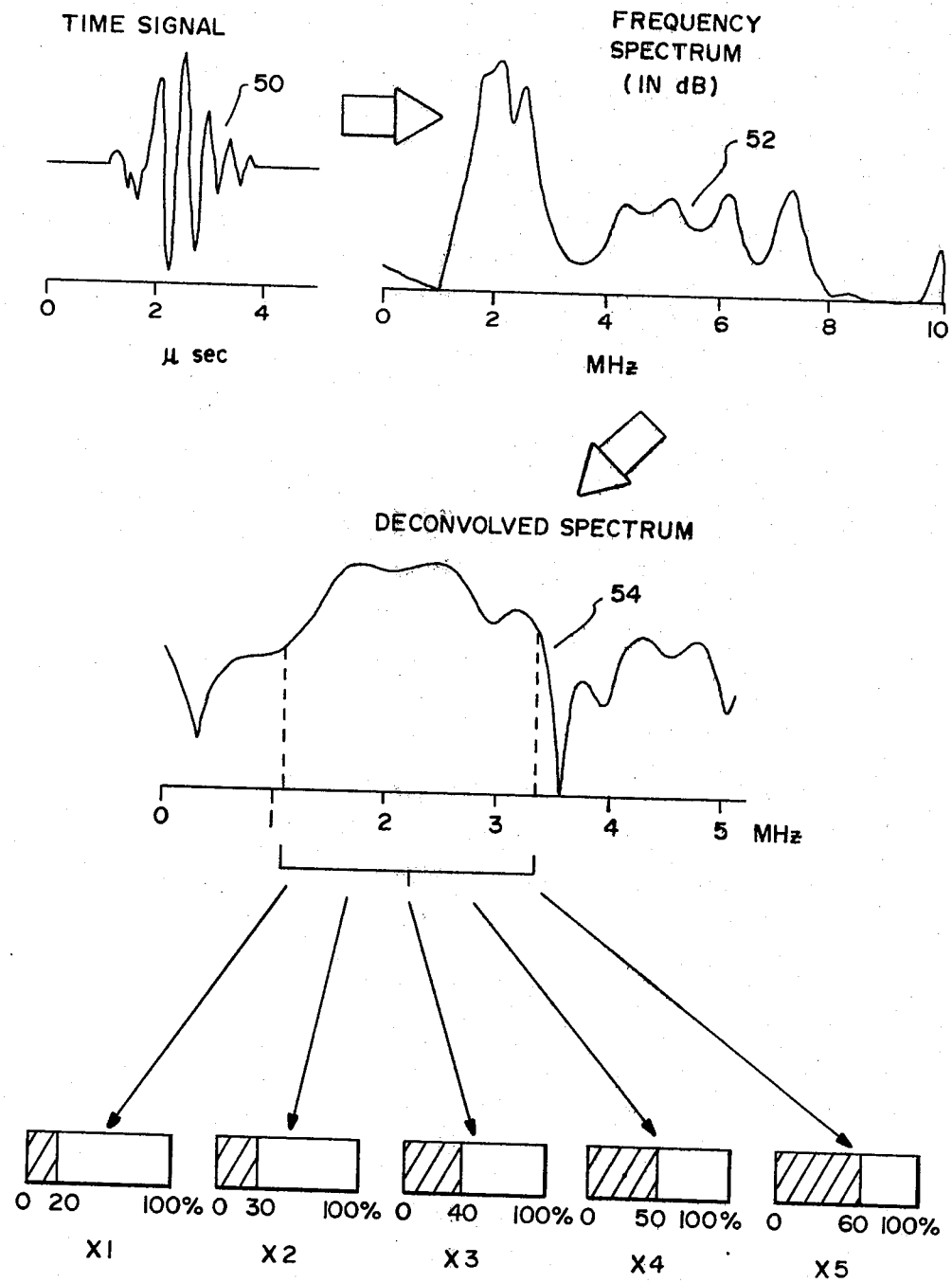
FIG.—5

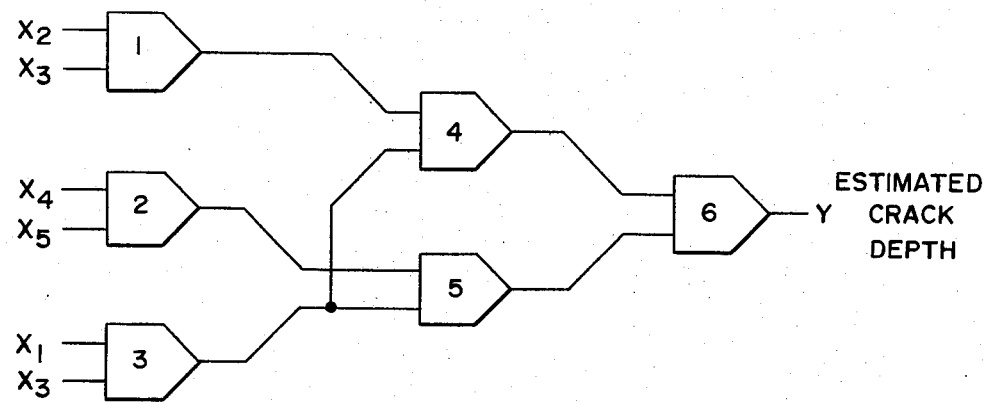
FIG.—6

METHOD OF MONITORING DEFECTS IN TUBULAR PRODUCTS

This invention relates generally to methods of analyzing defects in a product, and more particularly the invention relates to methods for monitoring a defect such as a crack in a product such as a steam pipe to assure safe operation of the product.

In steam driven electric power generation systems and particularly in nuclear power systems high pressure water or steam is used to transmit thermal energy from the source to turbine units by means of steel pipes. Such pipes typically have stress corrosion cracks in the vicinity of welded joints, and much interest has centered on the initiation and growth of such stress corrosion cracks. While the cause of such cracks in stainless steel is believed to be a combination of high surface residual stress, high oxygen content and sensitization, little is known about the growth rate of such cracks.

Such pipes are normally inspected by various techniques to identify the presence of cracks and to determine the effect thereof on use of the pipe. However, while analysis may indicate that a crack presents no hindrance to safe operation of the pipe, no assurance can be given that the crack will not grow and later become a fatal defect in the safe operation of the product.

Accordingly, an object of the present invention is a method of monitoring a defect such as a crack in a product such as a steel pipe.

Another object of the invention is a method of monitoring a defect in a product during periodic in-service inspection of the product.

A feature of the invention is the use of a statistical pattern recognition method called adaptive learning networks and ultrasonic techniques to determine changes in a defect.

Briefly, in accordance with the invention a defect such as a crack in a product such as a steel pipe is periodically monitored by applying ultrasonic waves to the product in close proximity to the defect and receiving reflected waves from the defect by means of a plurality of transducers. Electrical signals generated by the transducers are analyzed to determine changes therein which are indicative of changes in the defect.

More particularly, an adaptive learning model for the product and defect is established and the electrical signals are analyzed in accordance with the model. In a preferred embodiment the model is based on signal power ratios computed over several electrical signal frequency bands in a fixed frequency bandwidth. Differences in the power ratios as interpreted by the adaptive learning network model indicate changes in the size of the defect such as the length or depth of a crack.

The invention and objects and features thereof will be more fully understood from the following detailed description when taken with the drawing.

In the drawing, FIG. 1 is a perspective view of a section of a pipe having a stress corrosion crack therein.

FIG. 2 is a functional block diagram of data acquisition equipment for generating signals for use in analyzing a defect.

FIG. 3 is a representation of a plurality of transducers mounted on a tubular product for receiving reflected ultrasonic waves from a defect.

FIG. 4 is a flow diagram of the processing of electrical signals in accordance with the invention.

FIG. 5 is a representation of processed electrical signals and power ratio parameters generated therefrom.

FIG. 6 is a schematic of an adaptive learning network model using the power ratios of FIG. 5 to determine variations in a defect.

The importance of identifying defects such as cracks in critical mechanical structures has long been recognized in many industries such as the aircraft industry. Adaptive Learning Network modeling is one technique which has heretofore been employed to identify defects in mechanical structures.

Adaptive Learning Network (ALN) is a technique whereby a model is built based upon known parameters and postulated parameters of a system. The various parameters and relationships are used to develop a small, preprocessing computer program. This program is used to augment the stated parameters with new parameters defined in terms of the old parameters. Thus, by gathering data on the system the derived parameters can be defined in terms of the measured parameters. Through computer implementation the Adaptive Learning Network technique is used to construct a non-linear multinominal model function from the data. Each iteration of the ALN program generates a more complex mathematical function in which both the coefficients and the structure of the model are determined simultaneously. As described by Augustyn in "Manufacturing Applications of Adaptive Learning Networks" published by the Society of Manufacturing Engineers in 1967, adaptive learning networks may be applied to any process or system.

In accordance with the present invention adaptive learning network techniques are employed to monitor a defect in order to determine changes therein which can affect the structural reliability of the product. The application has particular applicability to monitoring identified cracks in water or steam pipes as used in electric power generation systems and the invention will be described therewith. However, it will be appreciated that the invention has wider applicability.

FIG. 1 is a perspective view of a portion of a steel pipe 10 having an inner surface 12 and an outer surface 14. A tensile stress crack 16 exists in the inner surface of pipe 10 as a result of thermal stresses created in forming a weld joint, for example. Such cracks often occur in steel pipes and are readily identified. While such cracks may make the pipe unsafe for use in transmission of high pressure, high temperature steam or water, many such cracks are structurally insignificant. However, due to various factors an insignificant crack can grow and impact the utility of pipe.

FIG. 2 is a functional block diagram of an ultrasonic RF data acquisition system which is useful in implementing the process in accordance with the invention. Ultrasonic waves are periodically introduced into pipe 20 in close proximity to a known crack or other defect by means of an ultrasonic pulser 22. Transducer means 24 on the surface of pipe 20 receives reflected ultrasonic waves from the pipe defect and generates electrical signals which are received by a receiver 26. The output of receiver 26 is converted to a digital output by analog to digital converter 28, and the digital signal from A/D converter 28 is recorded in an RF digital recorder 30. The analog signals from receiver 26 may be viewed on a scope 32 by converting the digital signals from A/D converter 28 back to analog signals by D/A converter 34.

The triggering and data recording function of the hardware is controlled by a suitable computer such as CPU 36. Apparatus for practicing the invention is readily available and does not constitute part of the invention. For example, the analog to digital converter and digital recorder may comprise a Biomation 8100 device. The pulser and receiver may comprise a Panametrics 5055 device and the digital recorder may comprise a Kennedy system 4000 cartridge type digital tape recorder. The transducers are preferably wide band having a 2.25 megahertz response.

In a preferred embodiment an array of 11 transducers are employed in receiving the reflected ultrasonic wave, as illustrated in FIG. 3. The five transducers shown generally at 40 are arranged on the outer surface of the pipe in axial alignment and spaced from the crack 42 having a length designated a, and the spacing of the tranducers is designated d. The plurality of transducers 44 and 46 are aligned circumferentially on the surface of the pipe at an angle of approximately 11° offset from the line of transducers 40 and the crack 42. By forming a synthetic array in the circumferential direction, the size of the crack along that dimension can be determined. The synthetic array in the axial direction allows for the radial depth of the crack to be determined. These arrays can be referred to as "broadside" and "endfire" arrays, respectively. The broadside arrays, centered at plus and minus 11°, can determine the length of the crack. The endfire array 40 is used to enhance the signal to noise ratio and permit measurement of the crack depth. In one embodiment the spacing between elements is 0.038 centimeters which allows for signal enhancement at a frequency of 2.25 megahertz, the center frequency of the transducers employed. An endfire array signal is obtained by delaying and summing each signal at the individual elements.

The frequency response of an ultrasonic signal scattered by a planar reflector in a host medium, which has no frequency-dependent attenuation, is:

$$P(f) = ah \left[ \frac{\sin(a \sin(\theta k_1 f))}{a \sin(\theta k_1 f)} \right] \left[ \frac{\sin(h k_2 f)}{h k_2 f} \right]$$

where a and h are the crack circumferential length and radial height, respectively, $k_1$ and $k_2$ are constants related to beam-refracted angle into the medium and its ultrasonic velocity, and $\theta$ is the angle made by the beam with the normal to the crack plane. The transmit and receive positions are assumed coincident in space; i.e., the pulse-echo mode is employed.

Some of the model's characteristics are:
(i) Existence of ripple structures in the power spectrum due to the crack dimensions a and h and whose periods in frequency are $1/ak_1\sin\theta$ and $1/hk_2$, respectively;
(ii) Existence of only a single ripple when the ultrasonic beam is at normal incidence to the crack plane; this ripple period is $1/k_2$ and it is independent of crack circumferential length a.
(iii) Frequency-dependent attenuation, proportional to $f^2$, which limits the bandwidth of the crack frequency response.

The signal response to normal incidence can be used in two ways: it allows for the crack radial depth h to be measured, and it can be used to deconvolve the response due to the crack radial length from the composite response to yield the circumferential length, a.

Since the circumferential length of the crack is usually greater than the radial length (i.e., aspect ratio, a/h, is greater than L0, there will be more ripple periods due to the former than due to the latter in a limited bandwidth, making the circumferential length size estimation correspondingly more accurate. Yet another phenomenom makes estimation of h less easy than a for actual data, and this is due to the "free surface" on the inner radius of pipe. This free surface, along with a potential defect in the weld heat affected zone (HAZ), forms a corner reflector. There will be phase changes, and hence ripple periods, due to interference caused by rays reflected from the free surface near the crack and reflected again by the defect towards the transducer.

FIG. 4 is a flow chart of the signal processing for determining the size and changes in size of the crack being monitored. The transducer signal from the "broadside" array is processed for a select frequency resolution and appropriate bandwidth. As above indicated, a center frequency of 2.25 megahertz was used in a preferred embodiment with a power spectrum of 0-4 megahertz. The array process signal is them deconvolved using a reference signal spectrum, $X_{ref}(f)$. The primary effect of deconvolution is to broaden the transducer signal frequency response. There is, however, a corresponding increase in signal noise level due to the broader bandwidth. Deconvolution of two signals in time is equivalent to the inverse transform of the Fourier transform of the ratio of the two signals; if the transducer is to be deconvolved from the observed scatter signal, its response is the divisor in the frequency domain division, as illustrated. The deconvolved signal is then applied to the ALN model for crack size determination.

FIG. 5 is a schematic illustrating signals in the flow chart of FIG. 4. The transducer signal as a function of time is given at 50 and the responsive signal in frequency domain is given at 52. After deconvolution the signal is shown at 54 from which five selected parameters, X1-X5, are determined based upon ratios of power in the frequency spectrum centered at 2.25 megahertz and 2.5 megahertz wide. These parameters are used with signal from only the end fired array.

FIG. 6 is a schematic of the ALN model including functional elements labeled 1-6 and using the parameters X1-X5 illustrated in FIG. 5. In this model the parameters are determined as follows:
X1 equal ratio of powers in lower 20% of the frequency spectrum to the upper 80% of the frequency spectrum;
X2 equal ratio of powers in the lower 30% of the frequency spectrum to the upper 70% of the frequency spectrum;
X3 equal ratio of powers in the lower 40% of the frequency spectrum to the upper 60% of the frequency spectrum;
X4 equal ratio of powers for the lower 50% of the frequency spectrum to the upper 50% of the frequency spectrum;
X5 equal ratio of powers in the lower 60% of the frequency spectrum to the upper 40% of the frequency spectrum.

Each of the functional elements 1-6 generates an output Y in response to the two inputs Xi and Xj as follows:

$$Y = W_0 + W_1 X_i + W_2 X_j + W_3 X_i X_j W_4 X_i^2 + W_5 X_j^2$$

The following network weighting coefficients for W0–W3 were employed for elements 1–6, as follows:

| ELEM | NETWORK WEIGHTING COEFFICIENTS | | | |
| --- | --- | --- | --- | --- |
| | Wφ | W1 | W2 | W3 |
| 1 | .φ376φ | −.φ1123 | .02979 | |
| 2 | .φ376φ | .φ293φ | −.φ1123 | |
| 3 | .φ3711 | −.φφ293 | −.φ1123 | |
| 4 | .φφ146 | 1.582φφ | −.62695 | |
| 5 | −.φφφ49 | .53369 | .48242 | |
| 6 | −.φ1φ26 | 2.φ83φ1 | −.6333φ | −4.16748 |

Of particular significance is the total dependence of the model on one parameter $x_3$, and to lesser extents on $x_4$ and $x_5$. Parameter $x_3$, the ratio of powers in the lower 40% to the uppr 60% of the frequency bandwidth, accounts for over 72% of the model's change in output due to changes in the five selected parameters. The next most influential parameter, $x_4$, the ratio in the lower 50% to the upper 50%, accounts for over 12.5% of the model's change. Combined, these two parameters account for over 84% of the model's change in output.

Whereas a positive change in $x_3$ results in a positive change in model output (i.e., modeled crack depth increases for increase in this parameter), a positive change in $x_4$ results in a negative change in model output. The effect on the model due to the former is six times greater than due to the latter, however. From a physical standpoint, parameter $x_3$ must be positively correlated to crack depth, because there would be a shift towards the lower frequencies of the lower spectrum, with a concomitant increase in $x_3$, as crack depth increases. Conversely, the parameter, $x_4$, the ratio of powers in the lower 50% of the frequency bandwidth, should be negatively correlated for increases in crack depth because of the shift in energy towards the lower frequencies. The signs of the partial derivatives agree with the above reasoning; the partial derivative with respect to $x_3$ is positive and with respect to $x_4$ is negative. That the mathematical model agrees with the physics is proof of the model's validity.

Additionally, $x_3$ and $x_4$, the two most important parameters selected by the model, differ in that the common band from 1.8 to 2.0 MHz appears in the denominator in the definition of $x_3$ and in the numerator in $x_4$. The change in sign of the partial derivatives, from positive with respect to $x_3$ to negative with respect to $x_4$, is due to a fairly large contribution to the total power due to the spectral band 1.8 to 2.0 MHz, the "swing" band between parameters $x_3$ and $x_4$. This band is close to the center frequency of the transducer where reliable measurements of spectral amplitude can be made and where signal-to-noise ratio is very large. Changes in the measured values of these two parameters are most likely to result from a phenomenological change (i.e., different cracks) than from a temporal change (random noise, error in measurement, etc.).

Thus, through use of ultrasonic techniques and by frequency domain analysis of reflected waves, an adaptive learning network model is devised for use in monitoring a crack or similar defect in a product and detecting any changes in the dimensions of the crack. The technique is particularly useful in monitoring steam pipes in electric power generation systems where structurally sound components are absolutely required. The method lends itself to in-service monitoring of components, thus requiring no shut-down of the system for testing.

While the invention has been described with reference to a specific embodiment and a specific application, the description is illustrative of the invention and is not to be construed as limiting the invention. Various modifications and applications will occur to those skilled in the art without departing from the true spirit and scope of the invention as defined by the appended claims.

What is claimed is:

1. The method of monitoring a defect such as a crack in a product such as steel pipe comprising the steps of
   (a) positioning a plurality of transducers on said product in predetermined positions relative to said defect, including a broadside array of transducers and an endfire array of transducers,
   (b) applying ultrasonic waves to said product in close proximity to said defect,
   (c) receiving waves reflected from said defect and generating electrical signals in response thereto, and
   (d) analyzing said electrical signals to determine changes therein which are indicative of changes in said defect by providing an adaptive learning network model for said product and defect and analyzing said electric signals in accordance with said model, said model being based on power ratios computed over several electrical signal frequency bands in a fixed frequency bandwidth.

2. The method of monitoring a defect as defined by claim 1 wherein said power ratios are based on
   the ratio of power in the lower 20% of the frequency bandwidth to the upper 80% of the frequency bandwidth,
   the ratio of power in the lower 30% of the frequency bandwidth to the upper 70% of the frequency bandwidth,
   the ratio of power in the lower 40% of the frequency bandwidth to the upper 60% of the frequency bandwidth,
   the ratio of power in the lower 50% of the frequency bandwidth to the upper 50% of the frequency bandwidth, and
   the ratio of power in the lower 60% of the frequency bandwidth to the upper 40% of the frequency bandwidth.

3. The method of monitoring a defect as defined by claim 1 or 2 wherein said step of analyzing said electrical signals includes processing said signals by deconvolution.

* * * * *